United States Patent [19]

Frackman et al.

[11] Patent Number: 5,508,187
[45] Date of Patent: Apr. 16, 1996

[54] IN VITRO PHAGE LAMBDA DNA PACKAGING SYSTEM

[75] Inventors: Susan G. Frackman, Shorewood; Phillip P. Franciskovich, Brown Deer; James F. Jolly, Glendale; Robert A. Luhm, Mequon; William A. Riedl, Grafton, all of Wis.

[73] Assignee: Pharmacia P-L Biochemicals, Inc., Milwaukee, Wis.

[21] Appl. No.: 173,743

[22] Filed: Dec. 23, 1993

[51] Int. Cl.⁶ ............................... C12N 1/20; C12N 7/00; C12N 15/09
[52] U.S. Cl. .................... 435/235.1; 435/172.3; 435/317.1
[58] Field of Search .................. 435/69.1, 71.2, 435/172.3, 183, 220, 235.1, 252.33, 320.1; 536/23.72

[56] References Cited

PUBLICATIONS

Kohler et al. (1990) Nuc. Acids Res. 18(10), 3007–3013.
Zierdt (1988) Appl. Environ. Microbiol 54(10), 2590.
S. Rosenberg, et al., 38 Gene 165–175 (1985).
S. Chow, et al., 60 Gene 277–289 (1987).
H. Murialdo, et al., 15 Nucl. Acids Res. 119–140 (1987).
D. Cue, et al., 90 Proc. Natl. Acad. Sci. USA 9290–9294 (1993).
Product Bulletin, Life Technologies, Inc. (1993).
Product Bulletin, Novagen (Admitted Prior Art).
Product Bulletin, Amersham (1993).
Product Bulletin, Stratagene (1993).
Product Bulletin, Promega (Admitted Prior Art).
B. Hohn, et al., 74 Proc. Natl. Acad. Sci. USA 3259–3263 (1977).
N. Sternberg, et al., 1 Gene 255–280 (1977).
L. Enquist, et al., 68 Meth. Enzymol. 281–298 (1979).
B. Hohn, 68 Meth. Enzymol. 299–326 (1979).
S. Rosenberg, 153 Meth. Enzymol. 95–103 (1987).
E. Gunther, et al., 21 Nucl. Acids Res. 3903–3904 (1993).

Primary Examiner—Mindy B. Fleisher
Assistant Examiner—Philip W. Carter
Attorney, Agent, or Firm—Quarles & Brady

[57] ABSTRACT

A bacterial preparation capable of packaging phage λ DNA is disclosed. This preparation is in lyophilized form and is stable at ambient temperature. In a preferred form, the preparation contains an over-expressed terminase protein, is prepared from the bacterial strain E. coli Cla [λ c/857 Sam7 Δ(cos-Nu1-A)::Kn$^r$]/λ pTER and is capable of a packaging efficiency of at least $1 \times 10^8$ pfu/µg wild type λ DNA. The present invention is also a method of creating a phage λ DNA packaging extract comprising the steps of preparing a bacterial extract capable of packaging phage λ and lyophilizing said extract.

7 Claims, 2 Drawing Sheets

IN VITRO PHAGE LAMBDA DNA PACKAGING SYSTEM

FIELD OF THE INVENTION

The present invention relates to methods of creating and propogating recombinant DNA molecules. Specifically, the present invention relates to methods of creating a recombinant bacteriophage lambda molecule and packaging that molecule in an extract that is stable at ambient temperature.

BACKGROUND

Bacteriophage lambda (phage λ) is known as a convenient vector with which to isolate recombinant DNA sequences. In general, a foreign DNA molecule is inserted into the phage λ genome and propagated along with the native phage λ sequences. In order to propogate the phage, a system must be developed to "package" the phage.

The first reports of in vitro phage λ DNA packaging systems were described in Sternberg, N., Triemeier, D., and Enquist, L., *Gene* 1:255–280, 1977 and Hohn, B. and Murray, K., *Proc. Natl. Acad. Sci. USA* 74:3259–3263, 1977. These systems were not high efficiency (greater than $1 \times 10^8$ pfu/µg wild type λ DNA) packaging systems.

Some early λ packaging systems relied on a combination of extracts to achieve the packaging function. However, it is more convenient to use a single extract. A single extract packaging system was first described in Rosenberg, S.M., Stahl, M.M., Kobayashi, I., and Stahl, F., *Gene*. 38:165–175, 1986. This paper described a single bacterial strain useful for in vitro packaging of λ DNA. The strain was an *E. coli* C strain that carried a prophage that was deleted for the nicking site of action of terminase, cosN. (The terminase multimer in phage λ is made up of two proteins that provide a number of functions in λ DNA packaging, such as DNA recognition, prohead binding, cos site cleavage and probably the entry of the DNA into the prohead.) This cos deletion prevents the packaging of the endogenous prophage. Therefore, packaging extracts made from this lysogen produce no background of packaged endogenous DNA. The C strain of *E. coli* lacks any known DNA restriction system, thereby eliminating the possibility that DNA packaged in this system will be biased by restriction of the DNA. The extract described by Rosenberg, et al. is prepared by concentration of the induced lysogen followed by freezing. The extract was stable only when stored at −70° C.

The use of a plasmid that overexpresses the terminase genes as a way of enhancing packaging extracts was first described in Muraldo, H., Davidson, A., Chow, S., and Gold, M., *Nucl. Acids Res.* 15:119–140, 1987 and Chow, S., Daub, E., and Muraldo, H., *Gene*. 60:277–289, 1987. These references describe the use of packaging extracts produced from two *E. coli* K12 lysogens supplemented by an extract of another *E. coli* K12 strain carrying a plasmid that expresses the terminase subunits. This system utilizes sonicated extracts of two different bacterial strains and a freeze/thaw lysate of a third strain. The packaging extracts are unstable at storage temperatures above −70° C.

Current procedures for making λ DNA packaging extracts from a single lysogen and from the two lysogen system are included in Sambrook, J., Fritsch, E.F., and Maniatis, T., *Molecular Cloning. A Laboratory Manual*, 2nd ed. Cold Spring Harbor Laboratory Press, Cold Spring Harbor, N.Y. 1989. 2.95–2.107. The procedure for making single lysogen extracts that is provided does not use sonication and is said to produce extracts with an efficiency of $0.2 \times 10^8 – 1 \times 10^8$ pfu/µg wild type λ DNA. The references describe storage at −70° C.

λ DNA packaging extracts are now commercially available from a number of companies at efficiencies of $1 \times 10^8 – 20 \times 10^8$ pfu/µg wild type λ DNA. All of the presently available packaging extracts are unstable during storage at temperatures above −70° C.

Therefore, a single-extract in vitro phage λ packaging system that is stable during storage at ambient temperature is needed.

SUMMARY OF THE INVENTION

The present invention is a bacterial extract capable of packaging phage λ DNA. This preparation is in a lyophilized form and is stable at ambient temperature.

In a preferred form, the preparation contains an overexpressed terminase protein. In a most preferred form, the bacterial strain is *E. coli* Cla [λ cI857 Sam7 Δ(cos-Nu1-A)::Kn$^r$]/λ pTER and the packaging efficiency of the extract is at least $1 \times 10^8$ pfu/µg wild type λ DNA.

The present invention is also a method of preparing a phage λ DNA packaging extract. This method comprises the steps of preparing a bacterial extract capable of packaging phage λ DNA and lyophilizing this extract.

In a preferred embodiment, the method of preparing a phage λ DNA packaging extract employs a bacterial extract that contains the terminase protein at a greater concentration than is found in a normal induced lysogen.

The object of the present invention is to provide a packaging extract that is stable at ambient temperature. This temperature stability will provide a great deal of convenience for a worker who does not wish to employ cold storage or does not have access to −70° C. freezers.

It is an advantage of the present invention that the phage λ DNA packaging system is a one-extract, high-efficiency system. A one extract system will provide convenience to a worker. A high-efficiency packaging system is necessary because searching for a desired foreign DNA sequence is often a statistical problem. A packaging extract must be able to provide an appropriate number of recombinant phage λ molecules.

Other objects, advantages, and features of the present invention will become apparent upon review of the specification, claims and drawings.

DESCRIPTION OF THE INVENTION

Figure 1:
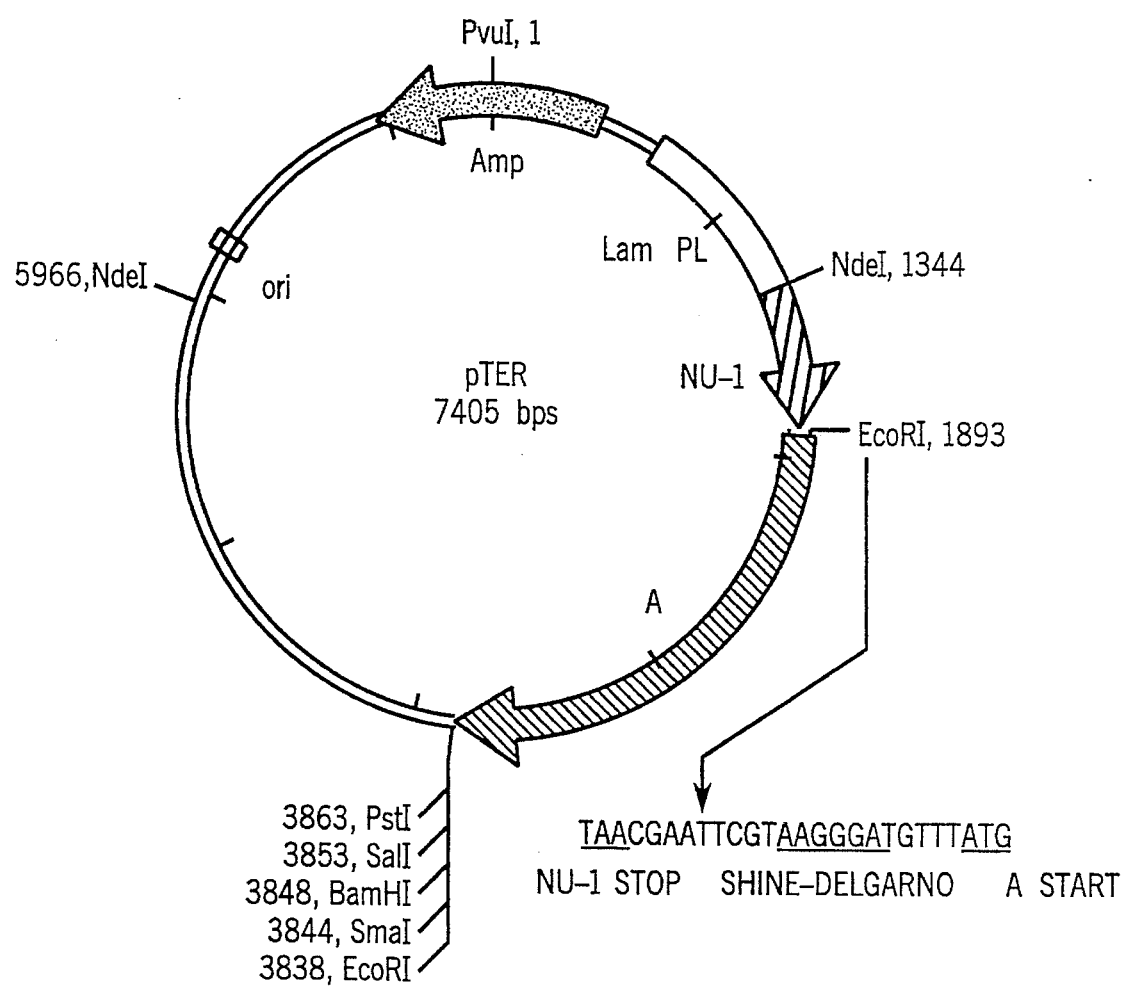
FIG. 1 is a schematic diagram of a plasmid capable of expressing terminase proteins.

Our objective in developing this in vitro λ DNA packaging system was to produce a high efficiency ($>1 \times 10^8$ pfu/µg wild type λ DNA) single extract system that is stable at ambient temperature. One major advantage of this system over other packaging systems is its stability at ambient temperature. By "ambient temperature stable" we mean that the extract maintains packaging activity of greater than $0.1 \times 10^8$ pfu/µg wild type λ DNA for at least 2 months when stored at normal room temperature (20°–25° C.). Preferably, the extract retains this efficiency when stored for 6 months at normal room temperature. Most preferably, the extract retains an efficiency of $1\times10^8$ pfu/μg wild type λ DNA after ambient storage. "Ambient temperature stable" also means that the stored extract retains at least 30% of the packaging efficiency of the original extract after room temperature storage for two months. Preferably, the extract retains at least 30% of the packaging efficiency of the original extract after room temperature storage for six months.

Therefore, the present invention is a λ DNA packaging system that is ambient-temperature stable. Preferably, this extract packages wild type λ DNA with an efficiency of greater than $1\times10^8$ pfu/μg wild type λ DNA. Most preferably, the packaging efficiency is at least $4\times10^8$ pfu/μg wild type λ DNA. Preferably, only a single extract is required for packaging λ DNA.

Although there are other single extract in vitro λ DNA packaging systems that have been described and are commercially available, the bacterial strain that is preferably used to produce the packaging extract of the present invention is different. Other single-tube in vitro DNA packaging systems use the strain constructed and described by Rosenberg, et al. (supra) one can obtain the Rosenberg, et al. strain from Susan Rosenberg, Institute of Molecular Biology, University of Oregon, Eugene, Oreg. Our preferred strain used in the Examples described below differs from the Rosenberg, et al. strain in that the entire cos site and the two terminase genes are deleted from the prophage in our preferred strain. This makes it possible to maintain a plasmid that carries the terminase genes in this strain without the possibility of homologous recombination between the prophage or plasmid that would result in loss or rearrangement of the phage genes. A plasmid carrying the terminase genes in the Rosenberg, et al. strain would be unstable due to homologous recombination between the prophage and plasmid genes.

The genotype of a bacterial strain preferably used to make the packaging extract is *E. coli* Cla [λ cI857 Sam7 Δ(cos-Nu1-A)::Kn$^r$]/λ pTER. (This strain has been deposited at American Type Culture Collection, Rockville, Md., at Accession No. ATCC 69501 on Dec. 3, 1993, 1993 under the terms and conditions of the Budapest Treaty.) E. coli Cla lacks any known DNA restriction system, thereby eliminating the possibility that libraries packaged in this system will be biased by restriction of the DNA. The thermoinducible defective λ prophage produces all of the structural proteins for proheads and tails. Because the prophage is deleted for the entire cos site, the prophage DNA cannot be packaged. This is particularly important because packaging extracts made from this lysogen produce no background of packaged endogenous DNA. Unlike the other systems that are presently available, the entire terminase nicking and binding site of the prophage is deleted, so the terminase cannot bind to the endogenous prophage DNA.

However, other bacterial packaging strains are also suitable for the present invention. It is preferred that the bacterial strain contain a prophage that is deleted for at least part of the terminase coding region or the DNA binding site of terminase (cos). To evaluate whether or not a particular bacterial strain is suitable for the present invention, one would first lyophilize the extract of the packaging strain as described in the Example sections. One would then store the packaging extract at ambient temperature (20°–25° C.) for a period sufficient to determine whether or not the extract was stable at ambient temperature. A suggested time period for a test is at least 2 months. After storage, one would use the sample extract to package both recombinant and wild-type λ DNA in a manner as described in the examples. An efficiency of greater than $1\times10^8$ pfu/μg wild type λ DNA would indicate a suitable strain.

Because the prophage of a strain suitable for the present invention does not contain a functioning terminase system, these proteins must be supplemented in the extract to achieve packaging. Preferably, a plasmid or other vector supplies the missing functions. The terminase is supplied on plasmid because it can be overexpressed from a plasmid as compared to expression from a lysogen. In a preferable form of the present invention the plasmid pTER overexpresses the genes for terminase (See FIG. 1). Referring to FIG. 1, over-expression of terminase is preferably achieved by placing the genes for Nu1 and A on a high copy number plasmid under the control of the pL promoter λ. The ribosome binding sites and initiation codons of the Nu1 and A genes on this plasmid may be altered to increase their expression. The thermoinducible repressor cI857 that is present in the prophage is responsible for repression of the plasmid terminase genes at low temperatures. A plasmid such as that depicted in FIG. 1 cannot be packaged because it does not have a cos site. There is no homology between the prophage and the plasmid that could result in loss or rearrangement of either the prophage or plasmid genes making this a relatively stable strain.

The bacterial extract of the present invention may be used to package λ wild-type and recombinant DNA prepared by many methods. Sambrook, et al., *Molecular cloning: a laboratory manual*, 2nd ed. Cold Spring Harbor Laboratory, Cold Spring Harbor, N.Y.

The bacterial strain of the present invention is preferably grown and induced by standard methods. The examples below give specific instructions as to how to grow and propogate the preferred strains. Other λ packaging strains are similarly manipulated. Copious literature, such as Sambrook, et al., exist to teach one of skill in the art how to propagate phage λ lysogens.

The extract is prepared by sonication and then lyophilized. We mean the term "lyophilized" to be synonymous with freeze-drying. In general, the extract is treated as other bacterial extracts would be for lyophilization or freeze-drying.

For the lyophilization process, single reaction aliquots of the extract are preferably frozen on dry ice in aluminum racks. (Freezing on dry ice produces more active extracts than freezing in liquid nitrogen, which has been used for all other packaging extract protocols.) The racks are placed on prechilled shelves in a subliminator. The vacuum is turned on. When the vacuum reaches 200 mTorr the condenser is turned on and sublimation typically proceeds with no shelf heat until the condenser reaches 50° C. This treatment is typically followed by 18 hours at a shelf temperature of 22° C. The vacuum is released and the tubes are sealed. At this point, the extract is stable at ambient temperatures.

After freeze-drying, the extract appears as a homogeneous, white, dense cake. It generally contains less than 5% residual water. The freeze-dried extract is very easily dissolved in water.

EXAMPLES

A. Bacterial Strain

The genotype of the bacterial strain we used to make the packaging extract in this system is *E. coli* Cla [λcI857 Sam7 Δ(cos-Nu1-A)::Kn$^r$] pTER. *E. coli* Cla lacks any known DNA restriction system. The thermoinducible defective λ prophage produces all of the structural proteins for proheads and tails. The prophage carries a deletion from the Bsb1 site at 48458 to the SphI site at 2212. A Kn$^r$ cassette replaces the deleted DNA. Because this deletion includes Nu1 and A (two proteins required for DNA packaging known as terminase) and the entire DNA site of action of terminase (cos), the prophage DNA cannot be packaged.

The bacteria contains a plasmid, pTER. The plasmid overexpresses the genes encoding the terminase proteins. The thermoinducible repressor cI857 that is present in the prophage is responsible for repression of the plasmid terminase genes at low temperatures. The pTER plasmid cannot be packaged because it does not have a cos site. There is no homology between the prophage and the plasmid that could result in loss or rearrangement of either the prophage or plasmid genes making this a relatively stable strain.

B. Construction of the terminase plasmid.

Both Nu1 and A gene sequences were amplified from λ DNA by PCR using modified primers specific to the 5' and 3' ends of each gene. The primer sequences used to amplify the A gene are reported at SEQ ID NO: 3 (5' sequence) and 4 (3' sequence). The primer sequences necessary to amplify the Nul gene are reported at SEQ ID NO: 5 (5' sequence) and 6(3' sequence). All PCR reactions were performed using the GeneAmp reagent kit and Perkin Elmer Cetus DNA thermal cycler as per the manufacturer's instructions. In addition to the gene-specific sequences, these primers also contained restriction sites necessary for directional cloning in the expression vector pJB2.2. In each case, the 5' PCR primers contained an Nde I site just 5' to the start codon producing the sequence CAT<u>ATG</u> where the ATG was the f-met initiation of translation. The 3' PCR primers contained an EcoRI restriction site just 3' of the translation terminator. This restriction site allowed for insertion of the cloned gene into pJB2.2 at the 5' Nde I site and the unique EcoRI site, thereby placing the gene in the proper orientation for expression of the gene off of the λ P$_L$ promotor. Prior to cloning into the expression vector, the PCR products were cloned non-directionally into pUC18 and partial sequence conformation was obtained. Both the Nu1 and A sequences were expressed individually as separate clones in pJB2.2. Each clone was induced by thermal induction and crude cell extracts were examined on denaturing polyacrylamide gels. Presence of subunit overexpression was observed in each case.

Upon confirmation of expression, the A subunit was modified in order to produce a tandem terminase vector whereby the A subunit would be expressed following the Nu-1 subunit as a polycystronic message transcribed from the same λP$_L$ promotor. Modification of the A subunit was essentially according to Murialdo, et al. (supra) (SEQ ID NO: 7 is a primer used to modify the A gene to make Nu1 A polycistronic region.) A short stretch of synthetic DNA was inserted by PCR on the 5' end of the A subunit (previously cloned in pUC18) consisting of an EcoRI restriction site and the ribosomal binding site D. The entire intervening sequence was (in brackets and at SEQ ID NO: 1):

EcoRI           A initiator

This construction produced a gene fragment consisting of the entire A subunit flanked by EcoRI sites with the attached intervening sequence containing the synthetic ribosomal binding site. The A subunit was then cloned directly 3' to Nu-1 by ligating the A subunit construct to the 3' EcoRI of pJB2.2 Nu-1 producing the following (and at SEQ ID NO: 2):

EcoRI           A initiator

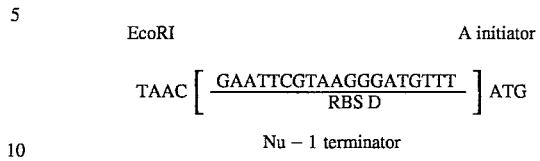

Nu − 1 terminator

The tandem terminase construction was confirmed by sequence. Both Nul and A were sequenced completely, and no errors were found. The plasmid was then induced to check expression of the terminase subunits. Proteins of the appropriate sizes were observed although at lower concentrations then the original subunits cloned and expressed separately.

C. Growth, induction and cell harvest of the bacterial culture.

The bacterial strain was grown and harvested as follows:

1. Inoculation of overnight culture of *E. Coli* Cla[λ c/857 Sam7 Δ(cos-Nu1-A)::Kn$^r$] pTER.

Kanamycin was added to a final concentration of 70 μg/ml and ampicillin was added to a final concentration of 100 μg/ml to 100 ml of NZM media (1% NZ amine, 0.5% NaCl, 10 mM MgSO$_4$) in a 500 ml flask. The flask with *E. coli* Cla[λ cI857 Sam7 Δ(cos-Nu1-A)::Kn$^r$] pTER was inoculated directly from a −70° C. glycerol stock of the bacteria. (The glycerol stock should not be allowed to thaw.) The overnight culture was grown at 32° C. with shaking.

2. Inoculation, growth and induction of the sonic extract culture.

Kanamycin was added to a final concentration of 70 μg/ml and ampicillin was added to a final concentration of 50 μg/ml to each of six 4 liter flasks containing 500 ml NZM. Each flask was inoculated with 10 mls of overnight culture. The cultures were grown at 32° C. with shaking (250–300 rpm) to an OD$_{600}$ of 0.35–0.4. 500 ml of NZM media at 64° C. were added to each flask. The incubator temperature was adjusted to 38° C. and the flasks continued incubating with shaking for 90 minutes.

3. Cell harvest.

The induced culture was poured into precooled sterile 500 ml centrifuge bottles and placed on ice immediately. The cells were pelleted by centrifugation in a precooled (4° C.) rotor and centrifuged at 4000×g for 10 minutes. The supernatant was discarded and the pellets placed on ice. 2 mls of cold sonication buffer (20 mM Tris.Cl pH 8.0, 1 mM EDTA pH 8.0, 5 mM β-mercaptoethanol) were then added to each bottle, and the pellets were resuspended gently but thoroughly. The resuspended cells were then pooled in a sterile precooled 50 ml beaker.

D. Sonication of induced culture.

The beaker with the resuspended cells was placed in a NaCl/H$_2$O/ice bath. A Vibra-cell sonicator was used to make the sonic extract. The cells were sonicated at 40% amplitude for 30 seconds. The sonicator was activated for 5 seconds followed by 10 second pause. This was repeated six times. The temperature was maintained below 5° C.

The extract was then cleared by centrifugation at 12K×g for 10 minutes at 4° C. The supernatant was transferred to a new tube and placed on ice. Phenylmethylsulfonyl fluoride was added to a final concentration of 0.1 mM and Aprotinin was added to a final concentration of 50 µg/ml. One sixth volume of packaging buffer (6 mM Tris-Cl pH 8.0, 50 mM spermidine, 50 mM potrescine, 20 mM $MgCl_2$, 30 mM ATP pH 7.0, 30 mM β-mercaptoethanol) was added to the extract, and the extract was mixed gently.

E. Dispensing of the packaging extracts.

25 µl were dispensed into the bottom of Sarstedt tubes. The tubes were placed in an aluminum rack that has been precooled on dry ice. The caps were placed on the tubes and tightened one quarter turn.

F. Lyophilization of the packaging extracts.

A Virtis 50 SRC sublimator was used for freeze-drying of the packaging extracts. The shelf temperature was cooled to below −50° C. The racks and tubes containing frozen extract were loaded into the sublimator. The door was closed and vacuum was turned on. The vacuum was allowed to drop to between 100 and 200 mTorr. The freezer was turned off and the condenser was turned on. The condenser was cooled to below −50° C. The shelf heat was set at 22° C. and turned on.

Sublimation proceeded for at least 18 hours. $N_2$ gas was bled into the chamber as the vacuum was released. The racks were removed and the tubes were quickly sealed. The tubes were stored in air-tight pouches with desiccant at ambient temperature.

Figure 2:
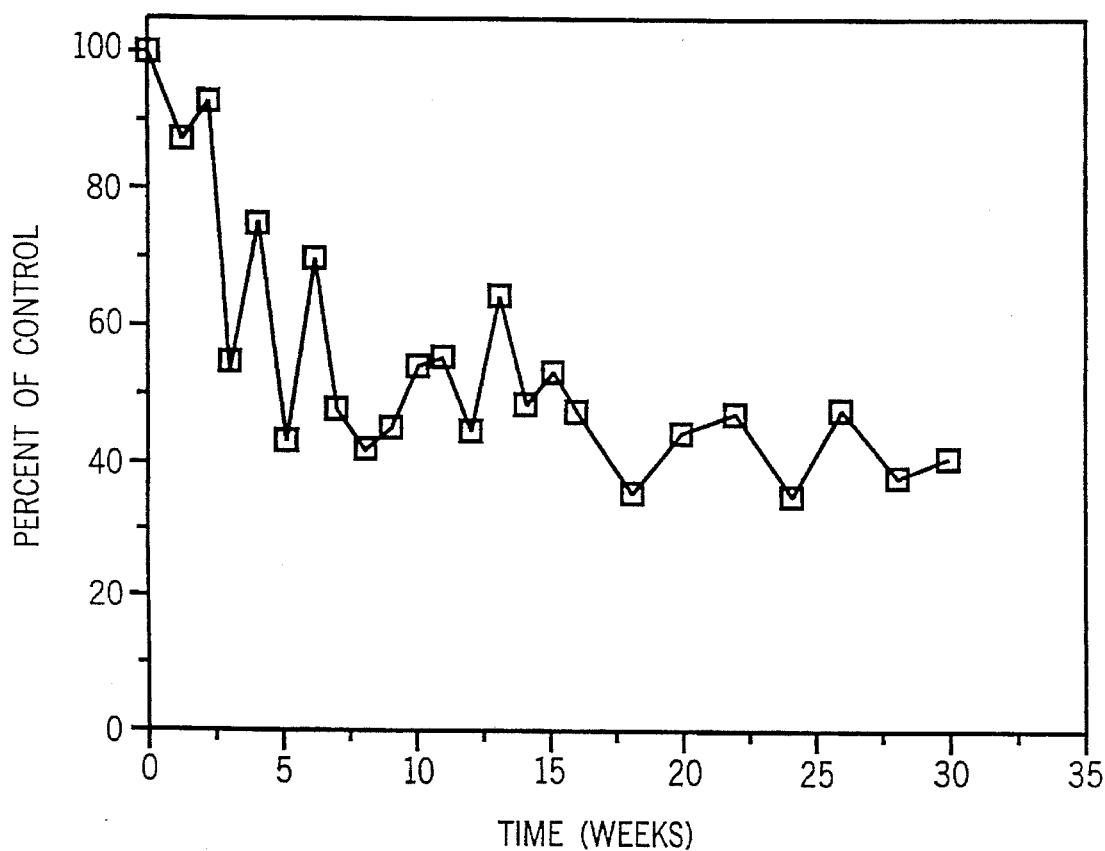
FIG. 2 is a graph of a stability study.

Stability studies were conducted with the lyophilized extract. FIG. 2 describes one of these studies. Referring to FIG. 2, at ambient temperature (20°–25° C.), the extract, initially at a packaging efficiency of $6.9 \times 10^8$ pfu/µg wild type λ DNA, loses approximately 50% of its activity. The activity remains at 40–60% of the initial activity for at least 30 weeks when stored at ambient temperature. Packaging efficiency immediately after drying must be at least $2.5 \times 10^8$ pfu/µg wild type λ DNA to have $1 \times 10^8$ pfu/µg wild type λ DNA after ambient temperature storage for greater than 1 month. All other packaging systems that are commercially available or have been described in the literature are unstable at storage temperatures above −70° C.

G. DNA packaging of wild type λ DNA and recombinant DNA.

The appropriate number of extracts were removed from the pouch. The unused extracts were resealed in the pouch. The dried extract was collected at the bottom of the tube by brief centrifugation if necessary.

To package recombinant λ DNA, 0.05–5.0 µg DNA in 1–8 µl of ligation buffer or TE was used for each packaging reaction. The DNA was then added to the dried packaging extract. Then sterile distilled $H_2O$ was added to 25 µl.

To package wild type λ DNA, 0.25 µg DNA was used. The λ DNA was added directly to the dried extract. Sterile distilled $H_2O$ to 25 µl was then added.

The tubes were centrifuged briefly to ensure that all of the rehydrated extract was in the bottom of the tube. No mixing was required. The packaging reactions were incubated 2 hrs. at room temperature (22° C.). 0.5 ml phage dilution buffer (SM buffer) and 2–3 drops of $CHCl_3$ were then added. The packaging reactions were mixed gently. The tubes were spun at top speed in a microfuge for 30 seconds. The lysate was transferred to a new tube and titered on the appropriate bacterial host. The lysate was stable for 7 days at 4° C. Packaging efficiency varied from $1 \times 10^8$ to $10 \times 10^8$ pfu/µg wild type λ DNA.

H. Other attempts at producing high efficiency ambient stable λ DNA packaging extracts.

Dried packaging extracts were made from a strain that was described in Rosenberg, et al. As described above, this strain is an *E. coli* C strain that carries a prophage that is deleted for part of the cos site. Terminase was supplied only by the induced prophage. The dried packaging extracts from this strain had packaging efficiencies of $0.1-1 \times 10^8$ pfu/µg wild type λ DNA. In an attempt to increase the packaging efficiency by increasing the amount of terminase present in the extracts, purified terminase (purchased from Takara Biochemical, Inc) was added before drying. This resulted in a 0–3-fold increase in packaging efficiency.

---

We claim:

1. In a method of preparing a phage λ packaging extract, the improvement comprising lyophilizing said extract to make a lyophilized extract.

2. The method of claim 1 wherein the lyophilized extract is stable during storage at ambient temperature.

3. The method of claim 1 wherein the packaging extract is prepared from a bacterial strain that overexpresses the terminase gene.

4. The method of claim 1 wherein the packaging extract is prepared from a bacterial strain of genotype *E. coli* Cla/λ pTER.

5. The method of claim 1 wherein the lyophilizing step comprises cooling the extract to below $-50°$ C. then vacuum drying the extract for at least 18 hours.

6. A bacterial phage λ DNA packaging extract preparation, wherein said preparation is in a lyophilized form and is stable at ambient temperature.

7. The preparation of claim 6 wherein the preparation is capable of packaging phage DNA at greater than $1 \times 10^8$ pfu/µg wild type λ DNA.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:1:

GAATTCGTAA GGGATGTTTA TG        2 2

( 2 ) INFORMATION FOR SEQ ID NO:2:

( i ) SEQUENCE CHARACTERISTICS:
        ( A ) LENGTH: 26 base pairs (B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO:2:

TAACGAATTC GTAAGGGATG TTTATG 26

(2) INFORMATION FOR SEQ ID NO:3:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO:3:

GTAGCCATAT GAATATATCG AACAGTCAGG TTAACAGGC 39

(2) INFORMATION FOR SEQ ID NO:4:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO:4:

GTCGGAATTC TCATTCATCC TCTCCGGATA AGGCACGG 38

(2) INFORMATION FOR SEQ ID NO:5:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO:5:

GTAGCCATAT GGAAGTCAAC AAAAAGCAGC TGGCTGACAT TTTCGG 46

(2) INFORMATION FOR SEQ ID NO:6:

(i) SEQUENCE CHARACTERISTICS:
(A) LENGTH: 47 base pairs
(B) TYPE: nucleic acid
(C) STRANDEDNESS: single
(D) TOPOLOGY: linear (ii) MOLECULE TYPE: Other Nucleic Acid (xi) SEQUENCE DESCRIPTION: SEQ ID NO:6:

GTAGAATTCG TTAACCTGAC TGTTCGATAT ATTCACTCAG CAACCCC 47

(2) INFORMATION FOR SEQ ID NO:7:

(i) SEQUENCE CHARACTERISTICS:
(A) LENGTH: 53 base pairs
(B) TYPE: nucleic acid
(C) STRANDEDNESS: single
(D) TOPOLOGY: linear (ii) MOLECULE TYPE: Other Nucleic Acid ( x i ) SEQUENCE DESCRIPTION: SEQ ID NO:7:

CCAGAATTCG TAAGGGATGT TTATGAATAT ATCGAACAGT CAGGTTAACA GGC    53